United States Patent [19]

Cushman et al.

[11] 4,154,937
[45] May 15, 1979

[54] HYDROXYCARBAMOYLALKYLACYL-PIPECOLIC ACID COMPOUNDS

[75] Inventors: David W. Cushman, West Windsor; Miguel A. Ondetti, Princeton, both of N.J.

[73] Assignee: E. R. Squibb & Sons, Inc., Princeton, N.J.

[21] Appl. No.: 918,882

[22] Filed: Jun. 26, 1978

Related U.S. Application Data

[60] Continuation-in-part of Ser. No. 768,003, Feb. 11, 1977, Pat. No. 4,128,653, which is a division of Ser. No. 657,793, Feb. 13, 1976, Pat. No. 4,052,511.

[51] Int. Cl.² .................................. C07D 211/60
[52] U.S. Cl. .................................. 546/221; 546/226; 546/242; 546/245
[58] Field of Search ................ 260/293.76, 293.86

[56] References Cited

U.S. PATENT DOCUMENTS

| | | | |
|---|---|---|---|
| 3,337,548 | 8/1967 | Kalopissis et al. | 260/293.86 |
| 4,046,889 | 9/1977 | Ondetti et al. | 260/293.86 |

*Primary Examiner*—Natalie Trousof
*Assistant Examiner*—Richard A. Schwartz
*Attorney, Agent, or Firm*—Lawrence S. Levinson; Merle J. Smith

[57] ABSTRACT

New hydroxycarbamoylalkylacyl derivatives of pipecolic acid which have the general formula

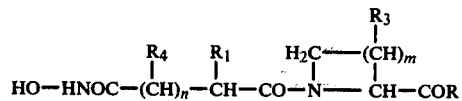

are useful as angiotensin converting enzyme inhibitors.

13 Claims, No Drawings

HYDROXYCARBAMOYLALKYLACYLPIPECOLIC ACID COMPOUNDS

CROSS-REFERENCE TO RELATED APPLICATIONS

This application is a continuation-in-part of application Ser. No. 768,003, filed Feb. 11, 1977 U.S. Pat. No. 4,128,653, issued Dec. 5, 1978, which is a division of application Ser. No. 657,793, filed Feb. 13, 1976, now U.S. Pat. No. 4,052,511, issued Oct. 4, 1977.

SUMMARY OF THE INVENTION

This invention relates to new carboxyalkylacylamino acids and related compounds which are derivatives of proline, pipecolic acid, azetidine-2-carboxylic acid and which have the general formula

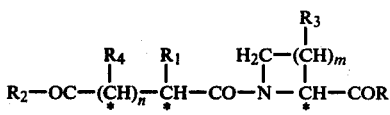

wherein
R is hydroxy, amino or lower alkoxy;
$R_1$ and $R_4$ each is hydrogen, lower alkyl or phenyl-lower alkyl;
$R_2$ is hydroxy, amino, hydroxyamino or lower alkoxy;
$R_3$ is hydrogen, hydroxy or lower alkyl;
m is 1 to 3;
n is 0 to 2.

The asterisks indicate asymmetric carbon atoms. The carbons in the acyclic side chain are asymmetric when $R_1$ or $R_4$ are other than hydrogen.

DETAILED DESCRIPTION OF THE INVENTION

The invention in its broad aspects includes derivatives of proline, pipecolic acid, azetidine-2-carboxylic acid and related compounds having formula I above. Within this broad group, because of their properties, certain subgroups are preferred over others.

Broadly preferred are those compounds of formula I wherein R is hydroxy or lower alkoxy, especially the first; $R_1$ is hydrogen or lower alkyl; $R_2$ is hydroxy; $R_3$ and $R_4$ each is hydrogen, m is 2 and n is 1 or 2, especially 2. $R_4$ is preferably on the carbon adjacent to the carbonyl of the terminal acid group.

Especially preferred are those compounds which are derived from proline and have the formula

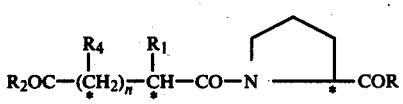

wherein
R is hydroxy or lower alkoxy;
$R_1$ is hydrogen, lower alkyl, especially methyl, or phenyl-lower alkyl, especially phenylmethyl;
$R_2$ is hydroxy, lower alkoxy, phenyl-lower alkoxy or hydroxyamino;
$R_4$ is hydrogen or lower alkyl, especially methyl; and
n is 1 or 2.

Within the group of compounds represented by formula II, the following are still more preferred subgroups in the order (a to n) of increasing preference to the compounds which are especially preferred embodiments:

(a) R is hydroxy
(b) n is 1
(c) n is 2
(d) $R_2$ is hydroxy
(e) $R_2$ is hydroxyamino
(f) $R_2$ is lower alkoxy
(g) $R_4$ is methyl
(h) $R_4$ is hydrogen
(i) $R_1$ is hydrogen or methyl
(j) R is hydroxy, $R_1$ is hydrogen or methyl
(k) R and $R_2$ each is hydroxy, $R_1$ and $R_4$ each is hydrogen or methyl and n is 1 or 2
(l) R and $R_2$ each is hydroxy, $R_1$ and $R_4$ each is hydrogen and n is 2
(m) R and $R_2$ each is hydroxy, $R_1$ is methyl, $R_4$ is hydrogen and n is 1
(n) R and $R_2$ each is hydroxy, $R_1$ is methyl, $R_4$ is hydrogen and n is 2

The stereoisomers in which the proline is in the L-form are especially preferred.

The lower alkyl groups represented by any of the variables include straight and branched chain hydrocarbon radicals from methyl to heptyl, for example, methyl, ethyl, propyl, isopropyl, butyl, isobutyl, t-butyl, pentyl, isopentyl and the like. The lower alkoxy groups are of the same kind having 1 to 7 carbons linked to oxygen, for example, methoxy, ethoxy, propoxy, isopropoxy, butoxy, isobutoxy, t-butoxy and the like. The $C_1$–$C_4$ members, especially $C_1$ and $C_2$ members, of both types are preferred. Phenylmethyl is the preferred phenyl-lower alkyl group.

The products of formula I and the preferred subgroups can be produced by various methods of synthesis. According to a preferred method, an acid of the formula

wherein $R_3$ is hydrogen, hydroxy or lower alkyl, e.g., proline, hydroxyproline, 4-methylproline, pipecolic acid, 5-hydroxy-pipecolic acid, azetidine-2-carboxylic acid or the like is coupled with a monoester of a malonic, succinic, glutaric acid, etc. of the formula

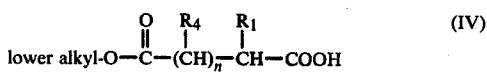

wherein $R_1$ and $R_4$ have the meanings defined above, by one of the known procedures in which the acid IV is activated, prior to reaction with the acid III, involving formation of a mixed anhydride, symmetrical anhydride, acid chloride, active ester, Woodward reagent K, N,N'-carbonylbisimidazole, EEDQ (N-ethoxycarbonyl-2-ethoxy-1,2-dihydroquinoline) or the like. [For a review of these methods, see Methoden der Organischen Chemie (Houben-Weyl) Vol. XV, parts 1 and 2 (1974)].

The product of this reaction is a compound of the formula

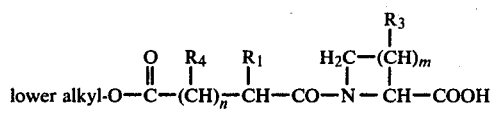

(V)

which is saponified, e.g., with a base like sodium hydroxide, in conventional manner to obtain the free diacid

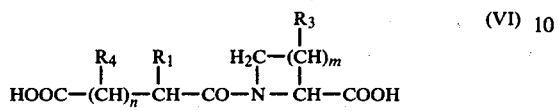

(VI)

Conversely the free acid can be esterified by conventional procedures.

As a modification of the above procedure, an ester of the acid of formula III, e.g., a lower alkyl ester, can be used in the reaction with the monoester of formula IV to obtain a compound of the formula

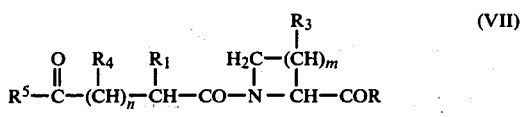

(VII)

wherein R and $R^5$ are ester groups, e.g., lower alkoxy. Other coupling reagents such as dicyclohexylcarbodiimide can be used in addition to those referred to above.

Ammonolysis of the acid of formula V yields the amide

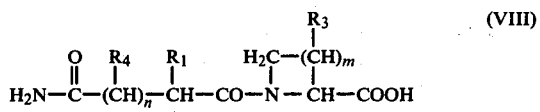

(VIII)

or hydroxyaminolysis of the acid V yields the hydroxamic acid

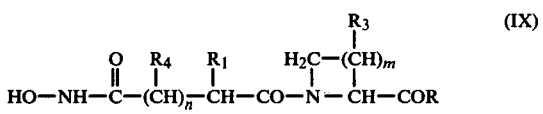

(IX)

The monoester starting materials of formula IV when n is 0 are obtained from the corresponding malonic acid diesters by the method described in Organic Syntheses 37, 34 (1957).

The succinic acid monoesters of formula IV (i.e., n is (1)) are prepared by alcoholysis of the corresponding substituted succinic anhydride. It is preferred to obtain products wherein the ester function is β to the alkyl side chain.

In order to obtain the required regiospecificity in the alcoholysis reaction, an alkylidene succinic anhydride is preferably used to obtain the starting monoester, e.g., an anhydride of the formula

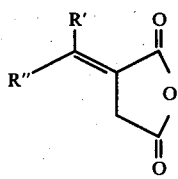

(X)

wherein

R' is hydrogen, lower alkyl or phenyl and

R" is hydrogen or lower alkyl.

This is treated with an alcohol ROH to obtain the product

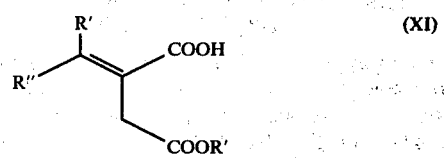

(XI)

then reduction with hydrogen yields the monoester

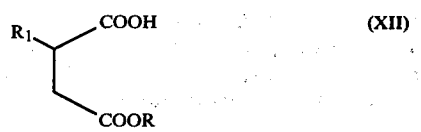

(XII)

Similarly, in the case of the glutaric acids (i.e., n is 2), alkylidene derivatives are used. When such alkylidene derivatives are not readily available, the substituted glutaric anhydride is subjected to alcoholysis followed by careful purification of the monoester by fractional crystallization of the dicyclohexylammonium salt.

Products of formula I have one asymmetric carbon and two if $R_1$ or $R_4$ are other than hydrogen. These carbon atoms are indicated by an asterisk in formula I. The compounds accordingly exist in diastereoisomeric forms or in racemic mixtures thereof. All of these are within the scope of the invention. The above described syntheses can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the amino acid constitutes the preferred isomeric form.

The compounds of this invention form basic salts with various inorganic and organic bases which are also within the scope of the invention. Such salts include ammonium salts, alkali metal salts like sodium and potassium salts (which are preferred), alkaline earth metal salts like the calcium and magnesium salts, salts with organic bases, e.g., dicyclohexylamine salt, benzathine, N-methyl-D-glucamine, hydrabamine salts, salts with amino acids like arginine, lysine and the like. The nontoxic, physiologically acceptable salts are preferred, although other salts are also useful, e.g., in isolating or purifying the product, as illustrated in the examples in the case of the dicyclohexylamine salt.

The salts are formed in conventional manner by reacting the free acid form of the product with one or more equivalents of the appropriate base providing the desired cation in a solvent or medium in which the salt is insoluble, or in water and removing the water by freeze drying. By neutralizing the salt with an insoluble acid like a cation exchange resin in the hydrogen form (e.g., polystyrene sulfonic acid resin—Dowex 50) or with an aqueous acid and extraction with an organic solvent, e.g., ethyl acetate, dichloromethane or the like, the free acid form can be obtained, and, if desired, another salt formed.

Additional experimental details are found in the examples which are preferred embodiments and also serve as models for the preparation of other members of the group.

The compounds of this invention inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance present which has been implicated as the causative agent in various forms of hypertension in various mammalian species, e.g., rats, dogs, etc. The compounds of this invention intervene in the renin→angiotensin I→angiotensin II sequence by inhibiting angiotensin converting enzyme and reducing or eliminating the formation of the pressor substance angiotensin II. Thus by the administration of a composition containing one or a combination of compounds of formula I or physiologically acceptable salt thereof, angiotensin dependent hypertension in the species of mammal suffering therefrom is alleviated. A single dose, or preferably two to four divided daily doses, provided on a basis of about 1 to 1000 mg. per kilogram per day, preferably about 10 to 100 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143 (1973). The substance is preferably administered orally, but parenteral routes such as subcutaneously, intramuscularly, intravenously or intraperitoneally can also be employed.

Compounds of formula I wherein R is other than hydroxy and $R_2$ is amino or lower alkyl are usually converted in the body to those having the two carboxy groups.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of formula I or physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials of the above type, a liquid carrier such as a fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples are illustrative of the invention and constitute especially preferred embodiments. All temperatures are in degrees celsius.

EXAMPLE 1

L-Proline tert.-butyl ester

L-Proline (230 g.) is dissolved in a mixture of water (1 l.) and 5 N sodium hydroxide (400 ml.). The solution is chilled in an ice bath, and under vigorous stirring, 5 N sodium hydroxide (460 ml.) and benzyloxycarbonyl chloride (340 ml.) are added in five equal aliquots during a half hour period. After one hour stirring at room temperature, the mixture is extracted twice with ether and acidified with concentrated hydrochloric acid. The precipitate is filtered and dried. Yield 442 g., m.p. 78°–80°.

The benzyloxycarbonyl-L-proline thus obtained (180 g.) is dissolved in a mixture of dichloromethane (300 ml.), liquid isobutylene (800 ml.) and concentrated sulfuric acid (7.2 ml.). The solution is shaken in a pressure bottle for 72 hours. The pressure is released, the isobutylene is allowed to evaporate and the solution is washed with 5% sodium carbonate, water, dried over magnesium sulfate and concentrated to dryness in vacuo, to obtain benzyloxycarbonyl-L-proline tert.butyl ester, yield 205 g.

Benzyloxycarbonyl-L-proline tert.butyl ester (205 g.) is dissolved in absolute ethanol (1.2 l) and hydrogenated at normal pressure with 10% Pd on carbon (10 g.) until only a trace of carbon dioxide is observed in the hydrogen exit gas (24 hours). The catalyst is filtered off and the filtrate is concentrated in vacuo at 30 mm Hg. The residue is distilled in vacuo, to obtain L-proline tert.butyl ester, b.p.$_{1mm}$ 50°–51°.

EXAMPLE 2

1-(2-Ethoxycarbonylpropanoyl)-L-proline tert.butyl ester

Monoethylmethylmalonate [prepared according to the procedure of Organic Syntheses, 37, 34 (1957)] (2.92 g.) and L-proline tert.-butyl ester (3.42 g.) are dissolved in dichloromethane (80 ml.). The solution is chilled with stirring in an ice bath. Dicyclohexylcarbodiimide (4.12 g.) is added and the mixture is stirred 15 minutes in the ice bath and 16 hours at room temperature. The precipitate is filtered off and the filtrate concentrated to dryness in vacuo. The residue is dissolved in ethyl acetate and washed with 5% aqueous potassium bisulfate, water, saturated sodium bicarbonate and water. The organic phase is dried over magnesium sulfate and concentrated to dryness in vacuo to obtain 1-(2-ethoxycarbonylpropanoyl)-L-proline tert.-butyl ester, yield 5.9 g.

EXAMPLE 3

1-(2-Ethoxycarbonylpropanoyl)-L-proline

The ester obtained in Example 2 (5.9 g.) is dissolved in trifluoroacetic acid, the solution is kept at room temperature for one hour, and then concentrated to dryness in vacuo. The residue is dissolved in a mixture of ethyl acetate and saturated aqueous sodium bicarbonate. The aqueous phase is acidified and extracted with ethyl acetate. The ethyl acetate layer is dried over magnesium sulfate and concentrated to dryness in vacuo to obtain 1-(2-ethoxycarbonylpropanoyl)-L-proline, yield 4.1 g.

EXAMPLE 4

1-(2-Carboxypropanoyl)-L-proline 1-(2-Ethoxycarbonylpropanoyl)-L-proline (4.1 g.) is dissolved in a mixture of N sodium hydroxide (51 ml.) and methanol (51 ml.). The solution is kept at room temperature for 6 hours and then concentrated to half volume in vacuo. Ion exchange resin (Dowex 50) (50 ml.) is added and the suspension applied to a column of 150 ml. of the same resin. The fractions containing the desired material (carboxyl reagent positive) are pooled and freeze dried to obtain to obtain 1-(2-carboxypropanoyl)-L-proline, yield 1.5 g.

EXAMPLE 5

1-(2-Carbamoylpropanoyl)-L-proline 1-(2-Ethoxycarbonylpropanoyl)-L-proline (2 g.) is dissolved in 10% methanolic ammonia and the mixture stored at room temperature in a pressure flask. When thin layer chromatographic analysis indicates that all the starting material has been converted to the amide, the mixture is concentrated to dryness, and the residual ammonium salt is converted to the free acid with ion exchange resin (Dowex 50 hydrogen form) to obtain 1-(2-carbamoylpropanoyl)-L-proline, yield 1.1 g.

EXAMPLE 6

1-(2-Hydroxycarbamoylpropanoyl)-L-proline sodium salt 1-(2-Ethoxycarbonylpropanoyl)-L-proline (2.4 g.) is dissolved in absolute ethanol (8 ml.). An ethanolic solution of hydroxylamine [prepared from hydroxylamine hydrochloride (0.7 g.) and sodium ethylate] is added, followed by a solution of sodium (0.23 g.) in absolute ethanol (8 ml.). After two hours the reaction mixture is added to vigorously stirred ether (500 ml.). The precipitate is filtered and dried to obtain 1-(2-hydroxycarbamoylpropanoyl)-L-proline sodium salt, yield 2 g. The free acid is prepared by treatment with an ion exchange resin (Dowex 50 in the hydrogen form).

EXAMPLE 7

1-(2-Ethoxycarbonyl-3-phenylpropanoyl)-L-proline tert.-butyl ester

By replacing monoethylmethylmalonate with monoethylbenzylmalonate [prepared by the procedure of R. Fraise-Julleen and C. Frejaville, *Bull. Soc. Chem. France*, 219 (1970)] in the procedure of Example 2, 1-(2-ethoxycarbonyl-3-phenylpropanoyl)-L-proline tert.-butyl ester is obtained.

EXAMPLE 8

1-(2-Ethoxycarbonyl-3-phenylpropanoyl)-L-proline

By substituting 1-(2-ethoxycarbonyl-3-phenylpropanoyl)-L-proline-L-tert.-butyl ester in the procedure of Example 3, 1-(2-ethoxycarbonyl-3-phenylpropanoyl)-L-proline, is obtained.

EXAMPLE 9

1-(2-Carboxy-3-phenylpropanoyl)-L-proline

By treating 1-(2-ethoxycarbonyl-3-phenylpropanoyl)-L-proline according to the procedure of Example 4, 1-(2-carboxy-3-phenylpropanoyl)-L-proline is obtained.

EXAMPLE 10

1-(2-Carbamoyl-3-phenylpropanoyl)-L-proline

By treating 1-(2-ethoxycarbonyl-3-phenylpropanoyl)-L-proline according to the procedure of Example 5, 1-(2-carbamoyl-3-phenylpropanoyl)-L-proline is obtained.

EXAMPLE 11

1-(2-(Hydroxycarbamoyl-3-phenylpropanoyl)-L-proline sodium salt

By treating 1-(2-ethoxycarbonyl-3-phenylpropanoyl)-L-proline according to the procedure of Example 6, 1-(2-hydroxycarbamoyl-3-phenylpropanoyl)-L-proline sodium salt is obtained.

EXAMPLE 12

1-(3-Methoxycarbonyl-2-methylpropanoyl)-L-proline tert.-butyl ester

3-Methoxycarbonyl-2-methylenepropanoic acid (36 g.) is dissolved in absolute ethanol (400 ml.) and hydrogenated over 10% Pd/C (3.6 g.) until no more hydrogen is absorbed. The catalyst is filtered off and the filtrate is concentrated to dryness in vacuo. The residue (37 g.) and L-proline tert.-butyl ester (42.7 g.) are dissolved in methylene chloride (750 ml.) and the solution is chilled with stirring in an ice bath. Dicyclohexylcarbodiimide (51.5 g.) is added and the mixture is stirred for 18 hours at room temperature. The precipitate is filtered off and the filtrate concentrated to dryness in vacuo. The residue is dissolved in ethyl acetate and washed neutral. The ethyl acetate is dried over magnesium sulfate and concentrated to dryness in vacuo. The residue is dissolved in ether and the acylurea side product is separated by filtration. The filtrate is concentrated to dryness in vacuo to obtain 1-(3-methoxycarbonyl-2-methylpropanoyl)-L-proline tert.-butyl ester, yield 64.7 g.

EXAMPLE 13

1-(3-Methoxycarbonyl-2-methylpropanoyl)-L-proline 1-(3-Methoxycarbonyl-2-methylpropanoyl)-L-proline tert.-butyl ester is dissolved in trifluoroacetic acid (150 ml.) and the solution is stored at room temperature for 1 hour. The trifluoroacetic acid is removed (mostly by evaporation) to dryness and the residue is reprecipitated from ether-hexane several times. Yield 18.3 g.

This material is dissolved in acetonitrile (10 ml.) and dicyclohexylamine (15 ml.) is added. The crystals are separated by filtration, suspended in acetonitrile (500 ml.) boiled for 5 minutes, cooled, filtered and dried. These crystals are resuspended in acetonitrile (450 ml.), boiled for five minutes, cooled, filtered and dried, to yield 13.6 g. m.p., 193°–194°, of the dicyclohexylamine salt of 1-(3-methoxycarbonyl-2-D-methylpropanoyl)-L-proline. From the first acetonitrile mother liquors, 6.2 g. of the dicyclohexylamine salt of 1-(3-methoxycarbonyl-2-L-methylpropanoyl-L-proline are obtained, m.p. 138°–139°. These salts are converted to the 1-(3-methoxycarbonyl-2-methylpropanoyl)-L-proline by treatment with an ion exchange resin (Dowex 50).

EXAMPLE 14

1-(3-Carboxy-2-methylpropanoyl)-L-proline

Each of the dicyclohexylammonium salts obtained in Example 13 (19.5 g.) is dissolved in a mixture of methanol (137 ml.) and N sodium hydroxide (137 ml.) and the solution is stirred at room temperature for five hours. The free diacid is isolated by chromatography on Dowex 50 ion exchange resin. The N-(3-carboxy-2-D-methylpropanoyl)-L-proline has m.p. 139°–141°; $[\alpha]_D^{25} = -70.5$ (c 2, EtOH). The N-(3-carboxy-2-L-methylpropanoyl)-L-proline has m.p. 132°–133° $[\alpha]_D^{25}$ −66.8° (c 1.1, EtOH).

EXAMPLE 15

1-(3-Carbamoyl-2-methylpropanoyl)-L-proline

By treating 1-(3-methoxycarbonyl-2-methylpropanoyl)-L-proline according to the procedure of Example 5, 1-(3-carbamoyl-2-methylpropanoyl)-L-proline is obtained.

EXAMPLE 16

1-(3-Hydroxycarbamoyl-2-methylpropanoyl)-L-proline

By treating 1-(3-methylcarbonyl-2-methylpropanoyl)-L-proline according to the procedure of Example 6, 1-(3-hydroxycarbamoyl-2-methylpropanoyl)-L-proline is obtained.

EXAMPLE 17

1-(3-Methoxycarbonyl-2-benzylpropanoyl)-L-proline tert.-butyl ester (a) 3-Methoxycarbonyl-2-benzylidenepropanoic acid 2-Carboxymethyl-3-phenylpropenoic acid (4.1 g.) and acetic anhydride (9 ml.) are heated in the steam bath for 70 minutes. The mixture is concentrated to dryness and the residue triturated with ether, yield 3.6 g. This anhydride is dissolved in 7 ml. of methanol and heated in the steam bath for 1 hour.

(b) Utilizing the procedure of Example 12 and replacing 3-methoxycarbonyl-2- methylenepropanoic acid with 3-methoxycarbonyl-2-benzylidenepropanoic acid, 1-(3-methoxycarbonyl-2-benzylpropanoyl)-L-proline tert.-butyl ester is obtained.

EXAMPLE 18

1-(3-Methoxycarbonyl-2-benzylpropanoyl)-L-proline

By treating 1-(3-methoxycarbonyl-2-benzylpropanoyl)-L-proline tert.-butyl ester according to the procedure of Example 13, 1-(3-methoxycarbonyl-2-benzylpropanoyl)-L-proline is obtained.

EXAMPLE 19

1-(3-Carboxy-2-benzylpropanoyl)-L-proline

By treating 1-(3-methoxycarbonyl-2-benzylpropanoyl)-L-proline according to the procedure of Example 14, 1-(3-carboxy-2-benzylpropanoyl)-L-proline is obtained.

EXAMPLE 20

1-(3-Carbamoyl-2-benzylpropanoyl)-L-proline

By treating 1-(3-methoxycarbonyl-2-benzylpropanoyl)-L-proline according to the procedure of Example 5, 1-(3-carbamoyl-2-benzylpropanoyl)-L-proline is obtained.

EXAMPLE 21

1-(3-Hydroxycarbamoyl-2-benzylpropanoyl)-L-proline

By treating 1-(3-methoxycarbonyl-2-benzylpropanoyl)-L-proline according to the procedure of Example 6, 1-(3-hydroxycarbamoyl-2-benzylpropanoyl)-L-proline is obtained.

EXAMPLE 22

1-(4-Carboxybutanoyl)-L-proline

Glutaric anhydride (4.6 g.) and L-proline (4.6 g.) are suspended in anhydrous pyridine (40 ml.) and refluxed for one hour. The mixture is concentrated to dryness in vacuo and the residue is dissolved in water and applied to a column of Dowex 50 (75 ml.) and eluted with water. The fractions containing the desired material (carboxyl reagent positive) are pooled and concentrated to dryness. The residue is dissolved in acetonitrile (50 ml.) and dicyclohexylamine is added until alkaline pH (wet indicator paper) is obtained. The crystals are filtered, dried and recrystallized from isopropanol (55 ml.) to yield the dicyclohexylamine salt of 1-(4-carboxylbutanoyl)-L-proline (14 g. m.p. 170°–172°).

The dicyclohexylamine salt is converted back to the acid with Dowex 50 resin in water.

EXAMPLE 23

1-(4-Methoxycarbonyl-2-methylbutanoyl)-L-proline tert.-butyl ester (a) 4-Methoxycarbonyl-2-methylbutanoic acid 2-Methylglutaric acid (14.6 g.) and acetyl chloride (26 ml.) are heated in the steam bath for one hour. The mixture is concentrated to dryness in vacuo and the residue evaporated twice from toluene. The residue is dissolved in methanol (4.7 ml.), heated on the steam bath for one hour and concentrated to dryness. The residue is dissolved in a mixture of ether (17 ml.), dicyclohexylamine (16.7 ml.) and hexane (83 ml.). The crystalline salt is filtered, stirred and treated with boiling ethyl acetate (75 ml.). The insoluble material is filtered off, and the filtrate is concentrated to one-third volume and chilled. The crystals are filtered and dried to yield 11.3 g. of 4-methoxycarbonyl-2-methyl butanoic acid dicyclohexylamine salt, m.p. 97°–99°. The salt is converted to the free acid by treatment with Dowex 50.

(b) 4-Methoxycarbonyl-2-methylbutanoic acid (3.1 g.) and L-proline tert.-butyl ester (3.78 g.) are dissolved in dichloromethane (40 ml.). The solution is chilled with stirring in an ice bath and dicyclohexylcarbodiimide (4.12 g.) is added. After stirring 15 minutes in the ice bath and 18 hours at room temperature, the precipitate is filtered off and the filtrate is concentrated to dryness in vacuo. The residue is chromatographed on a column of silica gel with chloroform to obtain 1-(4-methoxycarbonyl-2-methylbutanoyl)-L-proline tert.-butyl ester, yield 3.5 g.

EXAMPLE 24

1-(4-Methoxycarbonyl-2-methylbutanoyl)-L-proline 1-(4-Methoxycarbonyl-2-methylbutanoyl)-L-proline tert.-butyl ester (3.4 g.) is dissolved in trifluoroacetic acid (25 ml.) and the solution kept at room temperature for one hour. The trifluoroacetic acid is removed in vacuo and the residue is reprecipitated from ethyl-hexane several times. The residue is dissolved in acetonitrile (12 ml.) and 2 ml. of dicyclohexylamine is added.

The crystalline salt is isolated by filtration and recrystallized from acetonitrile to yield 18 g. of 1-(4-methoxycarbonyl-2-D-methylbutanoyl)-L-proline dicyclohexylamine salt, m.p. 174°-175°. From the mother liquors the 1-(4-methoxycarbonyl-2-L-methylbutanoyl)-L-proline isomer is also separated as the dicyclohexylamine salt. The salts are converted to the acids by treatment with Dowex 50.

EXAMPLE 25

1-(4-Carboxy-2-methylbutanoyl)-L-proline

Each of the dicyclohexylammonium salts obtained in Example 24 (1.3 g.) is dissolved in a mixture of methanol (9 ml.) and N sodium hydroxide (9 ml.). After five hours the acid is isolated by ion exchange chromatography on Dowex 50, yield 0.6 g. When the 1-(4-methoxycarbonyl-2-D-methylbutanoyl)-L-proline isomer of Example 24 is used, 1-(4-carboxyl-2-D-methylbutanoyl)-L-proline is obtained, and after crystallization from acetonitrile it has m.p. 154°-156°, yield 594 mg. $[\alpha]_D^{25}$ −99 (c 1.3, EtOH).

Utilizing the same procedure but starting with 1-(4-methoxycarbonyl-2-L-methylbutanoyl)-L-proline (750 mg.) the 1-(4-carboxy-2-L-methylbutanoyl)-L-proline [397 mg. m.p. 156°-157° $[\alpha]_D^{25}$ −22.5 (c, 1.5 EtOH) is obtained after crystallization from acetonitrile.

EXAMPLE 26

1-(4-Carbamoyl-2-methylbutanoyl)-L-proline

By treating 1-(4-methoxycarbonyl)-2-methylbutanoyl)-L-proline according to the procedure of Example 5, 1-(4-carbamoyl-2-methylbutanoyl)-L-proline is obtained.

Example 27

1-(4-Hydroxycarbamoyl-2-methylbutanoyl)-L-proline

By treating 1-(4-methoxycarbonyl)-2-methylbutanoyl)-L-proline according to the procedure of Example 6, 1-(4-hydroxycarbamoyl-2-methylbutanoyl)-L-proline is obtained.

EXAMPLE 28

1-(4-Methoxycarbonyl-2-benzylbutanoyl)-L-proline tert.-butyl ester

By treating benzylglutaric acid (CA 75, 48378e) according to the procedure of Example 23, 1-(4-methoxycarbonyl-2-benzylbutanoyl)-L-proline tert.-butyl ester is obtained.

EXAMPLE 29

1-(4-Methoxycarbonyl-2-benzylbutanoyl)-L-proline

By treating 1-(4-methoxycarbonyl-2-benzylbutanoyl)-L-proline tert.-butyl ester according to the procedure of Example 24, 1-(4-methoxycarbonyl-2-benzylbutanoyl)-L-proline is obtained.

EXAMPLE 30

1-(4-Carboxy-2-benzylbutanoyl)-L-proline

By treating 1(4-methoxycarbonyl-2-benzylbutanoyl)-L-proline according to the procedure of Example 25, 1-(4-carboxy-2-benzylbutanoyl)-L-proline is obtained.

EXAMPLE 31

1-(4-Carbamoyl-2-benzylbutanoyl)-L-proline

By treating 1-(4-methoxycarbonyl-2-benzylbutanoyl)-L-proline according to the procedure of Example 5, 1-(4-carbamoyl-2-benzylbutanoyl)-L-proline is obtained.

EXAMPLE 32

1-(4-Hydroxycarbamoyl-2-benzylbutanoyl)-L-proline

By treating 1-(4-methoxycarbonyl-2-benzylbutanoyl)-L-proline according to the procedure of Example 6, 1-(4-hydroxycarbamoyl-2-benzylbutanoyl)-L-proline is obtained.

EXAMPLE 33

1-(2-Ethoxycarbonylpropanoyl)-L-hydroxyproline

Monoethyl methylmalonate (1.46 g.) and N-hydroxysuccinimide (1.15 g.) are dissolved in ethyl acetate and the solution chilled with stirring in an ice bath. Dicyclohexylcarbodiimide (2.06 g.) is added and the mixture is stirred 15 minutes in an ice bath and overnight at room temperature. The precipitate is filtered off and the filtrate is concentrated to dryness. The residue is dissolved in pyridine (15 ml.) and added to a mixture of L-4-hydroxyproline (3.30 g.), sodium bicarbonate (2.5 g.) and water (15 ml.). After stirring for 18 hours at room temperature, water (60 ml.) is added and the solution is extracted with ethyl acetate. The aqueous phase is acidified (pH 2) and extracted with ethyl acetate. The ethyl acetate layer is dried over magnesium sulfate and concentrated to dryness to obtain 1-(2-ethoxycarbonyl-propanoyl)-L-hydroxyproline.

EXAMPLE 34

1-(2-Carboxypropanoyl)-L-hydroxyproline 1-(2-Ethoxycarbonylpropanoyl)-L-hydroxyproline is dissolved in a mixture of methanol (20 ml.) and N sodium hydroxide (20 ml.). After 6 hours the solvent is concentrated in vacuo to half volume and applied to a column of resin Dowex 50 (50 ml.) and eluted with water to obtain 1-(2-carboxypropanoyl)-L-hydroxyproline.

EXAMPLE 35

1-(2-Carboxypropanoyl)-L-azetidine-2-carboxylic acid

By substituting L-azetidine-2-carboxylic acid for the L-hydroxyproline in the procedure of Example 33, then continuing as in Example 34, 1-(2-ethoxycarbonylpropanoyl)-L-azetidine-2-carboxylic acid and 1-(2-carboxypropanoyl)-L-azetidine-2-carboxylic acid, respectively, are obtained.

EXAMPLE 36

1-(2-Carboxypropanoyl)-L-pipecolic acid

By substituting L-pipecolic acid for the L-hydroxyproline in the procedure of Example 33, then continuing as in Example 34, 1-(2-ethoxycarbonylpropanoyl)-L-pipecolic acid and 1-(2-carboxypropanoyl)-L-pipecolic acid, respectively are obtained.

EXAMPLE 37

1-(3-Carboxy-2-methylpropanoyl)-L-hydroxyproline

By substituting 3-methoxycarbonyl-2-methylpropanoic acid for the monoethyl methylmalonate in the procedure of Example 33, then continuing as in Example 34, 1-(3-methoxycarbonyl-2-methylpropanoyl)-L-hydroxyproline and 1-(3-carboxy-2-methylpropanoyl)-L-hydroxyproline are obtained.

EXAMPLE 38

1-(3-Carboxy-2-methylpropanoyl)-L-azetidine-2-carboxylic acid

By substituting 3-methoxycarbonyl-2-methylpropanoic acid for the monoethyl methylmalonate and L-azetidine-2-carboxylic acid for the hydroxyproline in the procedure of Example 33, then continuing as in Example 34, 1-(3-methoxycarbonyl-2-methylpropanoyl)-L-azetidine-2-carboxylic acid and 1-(3-carboxy-2-methylpropanoyl)-L-azetidine-2-carboxylic acid, respectively, are obtained.

EXAMPLE 39

1-(3-Carboxy-2-methylpropanoyl)-L-pipecolic acid

By substituting 3-methoxycarbonyl-2-methylpropanoic acid for the monoethyl methylmalonate and L-pipecolic acid for the hydroxyproline in the procedure of Example 33, then continuing as in Example 34, 1-(3-methoxycarbonyl-2-methylpropanoyl)-L-pipecolic acid and 1-(3-carboxy-2-methylpropanoyl)-L-pipecolic acid, respectively, are obtained.

EXAMPLE 40

1-(4-Carboxy-2-methylbutanoyl)-L-hydroxyproline

By substituting 4-methoxycarbonyl-2-methylbutanoic acid for the monoethyl methylmalonate in the procedure of Example 33, then continuing as in Example 34, 1-(4-methoxycarbonyl-2-methylbutanoyl)-L-hydroxyproline and 1-(4-carboxy-2-methylbutanoyl)-L-hydroxyproline, respectively, are obtained.

EXAMPLE 41

1-(4-Carboxy-2-methylbutanoyl)-L-azetidine-2-carboxylic acid

By substituting 4-methoxycarbonyl-2-methylbutanoic acid for the monoethyl methylmalonate, and L-azetidine-2-carboxylic acid for the hydroxyproline in the procedure of Example 33, then proceeding as in Example 34, 1-(4-methoxycarbonyl-2-methylbutanoyl)-L-azetidine-2-carboxylic acid and 1-(4-carboxy-2-methylbutanoyl)-L-azetidine-2-carboxylic acid, respectively, are obtained.

EXAMPLE 42

1-(4-Carboxy-2-methylbutanoyl)-L-pipecolic acid

By substituting 4-methoxycarbonyl-2-methylbutanoic acid for the monoethyl methylmalonate and L-pipecolic acid for the hydroxyproline in the procedure of Example 33, then proceeding as in Example 34, 1-(4-methoxycarbonyl-2-methylbutanoyl)-L-pipecolic acid and 1-(4-carboxy-2-methylbutanoyl)-L-pipecolic acid, respectively, are obtained.

EXAMPLE 43

1-(3-Carboxypropanoyl)-L-proline

Succinic anhydride (67 mmoles, 6.7 g.) is dissolved in 100 ml. of hot glacial acetic acid and cooled to room temperature. To this, while stirring (67 mmoles, 7.7 g.) L-proline is added. After 20 hours at room temperature, the reaction mixture is concentrated to dryness in vacuo. The residue is extracted three times with hot ethyl acetate and cooled to room temperature. To the pooled extracts containing the 1-(3-carboxypropanoyl)-L-proline, dicyclohexylamine is added and crystals form which are recrystallized from hot isopropanol, yield 11.3 g. The dicyclohexylamine salt has m.p. (170) 175°–177°.

EXAMPLE 44

1-(3-L-Carboxybutanoyl)-L-proline

Itaconic anhydride (154 mmoles) is dissolved in 100 ml. of glacial acetic acid, chilled in an ice bath and stirred. To this L-proline (17.7 g.) dissolved in 110 ml. of glacial acetic acid is added. After 5 minutes the ice bath is removed and the reaction mixture stored for three days at room temperature. The crude reaction mixture is taken up into 1 liter of acetonitrile and the insoluble haze filtered. The filtrate is taken to dryness in vacuo. About 26 g. of this residue, 1-(3-carboxy-3-methylenepropanoyl)-L-proline, is crystallized from water, yield 15.3 g., m.p. (82) 84°–85°, after drying for four hours at 50°, m.p. 125°–127°.

1-(3-Carboxy-3-methylenepropanoyl)-L-proline (3 g.) is dissolved in 50 ml. of 95% ethanol and 300 mg. of 10% Pd/C are added. The suspension is stirred under a positive hydrogen pressure for 18 hours. The catalyst is filtered off (Hyflo) and the filtrate concentrated to dryness in vacuo. The crude product is taken up into water and lyophilized. The lyophilate (DL) (3 g.) is taken up in 15 ml. of acetonitrile and two equivalents of dicyclohexylamine are added. The crude crystalline product is recrystallized from 60 ml. of isopropanol, yield, 3.17 g., m.p. (183) 187°–189°.

The dicyclohexylamine salt of 1-(3-L-carboxybutanoyl)-L-proline (3 g.) is treated with Dowex 50 ion exchange resin in water to isolate the free 1-(3-L-carboxybutanoyl)-L-proline which is lyophilized and the lyophilate is crystallized from acetonitrile-ether, yield, 691 mg., m.p. (122) 124°–125°.

EXAMPLE 45

1-(3-D-Carboxybutanoyl)-L-Proline

The mother liquors from the crystallization of the dicyclohexylamine salt in Example 44 (isopropanol) are concentrated to dryness and crystallized from acetonitrile, yield 3.2 g., m.p. (155) 160°–165°. This salt (3 g.) is dissolved in 15 ml. of water and 15 ml. of Dowex 50 ion exchange resin is added to adjust the pH below 7. This is applied to a 20 ml. column of the same resin that has been water washed. The product is eluted with water and those fractions that are carboxyl-reagent positive are lyophilized, yield 1.08 g. of 1-(3-D-carboxybutanoyl)-L-proline.

EXAMPLE 46

1-(3-Carboxy-3-benzylpropanoyl)-L-Proline

Benzylidenesuccinic anhydride (1.88 g.) is suspended in 20 ml. of anhydrous pyridine. To this L-proline (1.15 g.) is added and heated on the steam cone for 2.5 hours. It turns dark immediately. After cooling to room temperature an insoluble precipitate is filtered (m.p. 232°–233°) and the filtrate concentrated to dryness in vacuo. The residue is extracted with ether and the ether decanted off. The residue is taken up into ethyl acetate and washed with 5% potassium bisulfate and water. The ethyl acetate extracts are filtered and concentrated to dryness in vacuo. The crude product, 1-(3-carboxy-3-benzylidenepropanoyl-L-proline, is triturated with ether and after 48 hours yields 2.0 g., m.p. 132°–135°.

The crude material (1.9 g.) is taken up into 30 ml. of 95% ethanol and 200 mg. 10% Pd/C. This is stirred under positive hydrogen pressure for 18 hours. The reaction mixture is filtered through Hyflo and the filtrate concentrated to dryness in vacuo, yield 1.9 g. This is purified on a diethylaminoethyl Sephadex column with ammonium bicarbonate, yield 1.4 g. This ammonium salt is converted to the free acid 1-(3-carboxy-3-benzylpropanoyl)-L-proline through a column of Dowex 50 resin with aqueous methanol (8:2), yield 1.3 g. This is applied to a silica gel (70-230 mesh) column in chloroform (60); methanol (40) and 38% acetic acid (20), eluted with the same, and lyophilized, yield 1.1 g.

EXAMPLE 47

1-(4-Carboxy-3-methylbutanoyl)-L-Proline (isomer A)

3-Methylglutaric anhydride (1.28 g.) and L-proline tert.-butyl ester (1.88 g.) are stirred in 5 ml. of dry tetrahydrofuran in an ice bath for 5 minutes. The bath is removed and the reaction proceeds at room temperature for 3 hours. A crystalline precipitate forms immediately. Ether (10 ml.) is added and the crystals are filtered, yield 1.45 g., m.p. 168°-170°.

The 1-(4-carboxy-3-methylbutanoyl)-L-proline tert.-butyl ester thus obtained is dissolved in 10 ml. of trifluoroacetic acid and stored for 1 hour at room temperature, concentrated to dryness, taken up into water and lyophilized. The lyophilate is taken up into 10 ml. of water and applied to 55 ml. of Dowex 50 resin and eluted with water. Those carboxyl reagent positive fractions that do not give the typical trifluoroacetic acid color are pooled and lyophilized, yield 1.03 g. of 1-(4-carboxy-3-methylbutanoyl)-L-proline. The dicyclohexylamine salt prepared as in Example 22, melts at 170°-172°.

EXAMPLE 48

1-(4-Carboxy-3-methylbutanoyl)-L-proline (isomer B)

3-Methylglutaric anhydride (1.28 g.) and L-proline tert.-butyl ester (1.88 g.) in 5 ml. of dry tetrahydrofuran are stirred in an ice bath for 5 minutes. The bath is removed. After 3 hours, 10 ml. of ether are added. The crystalline precipitate 1-(4-carboxy-3-methylbutanoyl)-L-proline tert.-butyl ester (isomer A) is filtered and the filtrate concentrated to dryness in vacuo. The dicyclohexylamine salt is prepared in isopropyl ether 1.40 g. (m.p. 97°-98°). This salt is converted to the free acid through distribution between ethyl acetate and 5% potassium bisulfate, yield 922 mg.

The above ester is taken up into 10 ml. of trifluoroacetic acid and stored for 1 hour at room temperature. It is then concentrated to dryness in vacuo, taken into water, and lyophilized. The lyophilate is taken up into 10 ml. of water and applied to 54 ml. of Dowex 50 resin and eluted with water. Those COOH reagent positive fractions that do not give the typical trifluoroacetic acid color, are pooled and lyophilized, to give 1-(4-carboxy-3-methylbutanoyl)-L-proline (isomer B), yield 640 mg. The dicyclohexylamine salt is prepared as in Example 22, m.p. 189°-191°.

EXAMPLE 49

1-(4-Carboxy-4-methylbutanoyl)-L-Proline (a) 2-Methyl-4-benzyloxycarbonylbutyric acid 2-Methylglutaric acid (14.61 g.) is heated on the steam cone for 1 hour with 26 ml. of acetyl chloride, then concentrated to dryness in vacuo and toluene removed twice in vacuo. To the above crystalline solid, 12.5 ml. of benzyl alcohol are added and heated for one hour on the steam cone. The crude 26.5 g. of 2-methyl-4-benzyloxycarbonylbutyric acid is applied to a silica gel column in chloroform and eluted with the same. The dicyclohexylamine salt is prepared as in Example 22 yielding 18 g., m.p. 84°-85°. This is converted to 10.2 g. of free acid in ethyl acetate and 5% potassium bisulfate.

(b) 4-Methyl-4-methoxycarbonylbutyric acid

The benzyl ester from part a (10.2 g.) is taken up into 20 ml. of methanol and treated with excess ethereal diazomethane for 1 hour at room temperature. It is concentrated to dryness in vacuo.

This methyl ester (10.7 g.) is dissolved in 150 ml. of 95% ethanol and reduced under positive hydrogen pressure with 1 g. of 10% Pd/C for 18 hours. It is filtered through Hyflo and the filtrate concentrated to dryness in vacuo to obtain 6.8 g. of 4-methyl-4-methoxycarbonylbutyric acid.

(c) 1-(4-Carboxy-4-methylbutanoyl)-L-Proline

The reduction product from part b (6.8 g.) and L-proline tert.-butyl ester (8.0 g.) are dissolved in 85 ml. of methylene chloride and stirred in an ice bath. To this 8.8 g. of dicyclohexylcarbodiimide is added. After 15 minutes the bath is removed and the reaction proceeds overnight at room temperature. The dicyclohexylurea is filtered off and the filtrate concentrated to dryness in vacuo. The 1-(4-carboxy-4-methylbutanoyl)-L-proline tert.-butyl ester is taken up into ethyl acetate and washed with 5% potassium bisulfate, water, saturated sodium bicarbonate, water, dried over magnesium sulfate and taken to dryness in vacuo, yield 14.0 g.

The tert.-butyl ester thus obtained (14.0 g.) is treated for 1 hour with 75 ml. of trifluoroacetic acid and concentrated to dryness in vacuo. This is treated 2 times with ether-hexane to remove excess trifluoroacetic acid. The crude product is extracted into 150 ml. of saturated sodium bicarbonate and 250 ml. ethyl acetate. The extracts are again washed with saturated sodium bicarbonate. The aqueous fraction is acidified to pH 2 with concentrated hydrochloric acid, saturated with sodium chloride, extracted 4 times with ethyl acetate, washed once with saturated sodium chloride, dried over magnesium sulfate and concentrated to dryness in vacuo. The dicyclohexylamine salt is prepared in ether and recrystallized from ethyl acetate, yield 9.3 g., m.p. (120) 132°-133°. This salt is converted to the free acid, 1-(4-carboxy-4-methylbutanoyl)-L-proline.

The dicyclohexylamine salt (8.7 g.) is dissolved in 60 ml. of methanol and 60 ml. sodium hydroxide are added while stirring. To this 100 ml. of Dowex 50 resin is added to make the pH acid. This is applied to a 300 ml. column of Dowex 50 resin and eluted with water. Those fractions which are COOH-reagent positive are pooled and lyophilized to obtain 4.78 g. of 1-(4-carboxy-4-methylbutanoyl)-L-proline.

EXAMPLE 50

1-(3-Methoxycarbonyl-2-methylpropanoyl)-L-prolineamide 1-(3-Methoxycarbonyl-2-methylpropanoyl)-L-proline (2.4 g.) is dissolved in a mixture of dichloromethane (50 ml.) and triethylamine (1.4 ml.). The solution is chilled in an ice water bath and isobutylchloroformate (1.36 g.) is added while the mixture is stirred. After 10 minutes ammonia (gas) is bubbled through the solution, still in the ice bath, for fifteen minutes. The reaction mixture is stirred for one hour at room temperature, diluted with methylene chloride (100 ml.) and washed with water, 0.1 N hydrochloric acid, water, and dried over magnesium sulfate. The solvent is removed in vacuo to yield 1-(3-methoxycarbonyl-2-methylpropanoyl)-L-prolineamide.

EXAMPLE 51

1-(3-Carboxy-2-methylpropanoyl)-L-proline 1-(3-Methoxycarbonyl)-2-methylpropanoyl)-L-proline amide (1.2 g.) is dissolved in a mixture of methanol (10 ml.) and N sodium hydroxide (15 ml.). The mixture is stirred at room temperature and checked by electrophoresis every hour until disappearance of the starting ester is observed. The solution is neutralized with normal hydrochloric acid and concentrated in vacuo to half volume. This solution is applied in a column of ion exchange resin Dowex 50 and eluted with water. The fractions that give a positive carboxyl test are pooled and freeze dried to yield 1-(3-carboxy-2-methylpropanoyl)-L-proline.

EXAMPLE 52

1-(3-Carboxy-2-methylpropanoyl)-4-methyl-L-proline

By substituting 3-methoxycarbonyl-2-methylpropanoic acid for the monoethyl methylmalonate and 4-methyl-L-proline for the hydroxyproline in the procedure of Example 33, then continuing as in Example 34, 1-(3-methoxycarbonyl-2-methylpropanoyl)-4-methyl-L-proline and 1-(3-carboxy-2-methylpropanoyl)-4-methyl-L-proline, respectively, are obtained.

EXAMPLE 53

1-(3-Carboxy-2-methylpropanoyl)-5-hydroxy-L-pipecolic acid

By substituting 3-methoxycarbonyl-2-methylpropanoic acid for the monoethyl methylmalonate and 5-hydroxy pipecolic acid for the hydroxyproline in the procedure of Example 33, then continuing as in Example 34, 1-(3-methoxycarbonyl-2-methylpropanoyl)-5-hydroxy-L-pipecolic acid and 1-(3-carboxy-2-methylpropanoyl)-5-hydroxy-L-pipecolic acid, respectively, are obtained.

EXAMPLE 54

1-(4-Carboxy-2-methylbutanoyl)-4-methyl-L-proline

By substituting 4-methoxycarbonyl-2-methylbutanoic acid for the monoethyl methylmalonate and 4-methyl-L-proline for the hydroxy proline in the procedure of Example 33, then proceeding as in Example 34, 1-(4-methoxycarbonyl-2-methylbutanoyl)-4-methyl-L-proline and 1-(4-carboxy-2-methylbutanoyl)-4-methyl-L-proline, respectively, are obtained.

EXAMPLE 55

1-(4-Carboxy-2-methylbutanoyl)-5-hydroxy-L-pipecolic acid

By substituting 4-methoxycarbonyl-2-methylbutanoic acid for the monoethyl methylmalonate and 5-hydroxy-L-pipecolic acid for the hydroxy proline in the procedure of Example 33, then proceeding as in Example 34, 1-(4-methoxycarbonyl-2-methylbutanoyl)-5-hydroxy-L-pipecolic acid and 1-(4-carboxy-2-methylbutanoyl)-5-hydroxy-L-pipecolic acid, respectively, are obtained.

EXAMPLE 56

1-(4-Methoxycarbonyl-2-methylbutanoyl)-L-prolineamide

By substituting the 1-(4-methoxycarbonyl-2-methylbutanoyl)-L-proline of Example 24 for the 1-(3-methoxycarbonyl-2-methylpropanoyl)-L-proline in the procedure of Example 50, 1-(4-methoxycarbonyl-2-methylbutanoyl)-L-prolineamide is obtained.

EXAMPLE 57

By substituting for the 1-(2-ethoxycarbonylpropanoyl)-L-proline in the procedure of Example 6, respectively, the 1-(2-ethoxycarbonylpropanoyl)-L-pipecolic acid of Example 36, 1-(3-methoxycarbonyl-2-methylpropanoyl)-L pipecolic acid of Example 39, 1-(4-methoxycarbonyl-2-methylbutanoyl)-L-pipecolic acid of Example 42, 1-(3-methoxycarbonyl-2-methylpropanoyl)-5-hydroxy-L-pipecolic acid of Example 53, or 1-(4-methoxycarbonyl-2-methylbutanoyl)-5-hydroxy-L-pipecolic acid of Example 55, there are obtained, respectively, 1-(2-hydroxycarbamoylpropanoyl)-L-pipecolic acid,
1-(4-hydroxycarbamoyl-2-methylbutanoyl)-L-pipecolic acid,
1-(3-hydroxycarbamoyl-2-methylpropanoyl)-5-hydroxy-L-pipecolic acid,
1-(4-hydroxycarbamoyl-2-methylbutanoyl)-5-hydroxy-L-pipecolic acid and their sodium salts.

The racemic forms of the final products in each of the foregoing examples are produced by utilizing the DL-form of the starting amino acid instead of the L-form.

Similarly the D-form of the final products in each of the foregoing examples is produced by utilizing the D-form of the starting amino acid instead of the L-form.

EXAMPLE 58

1000 tablets each containing 100 mg. of 1-(4-carboxy-2-methylbutanoyl)-L-proline are produced from the following ingredients:

| | | |
|---|---|---|
| 1-(4-Carboxy-2-methylbutanoyl)-L-proline | 100 | g. |
| Corn starch | 50 | g. |
| Gelatin | 7.5 | g. |
| Avicel (microcrystalline cellulose) | 25 | g. |
| Magnesium stearate | 2.5 | g. |

The 1-(4-carboxy-2-methylbutanoyl)-L-proline and corn starch are admixed with an aqueous solution of the gelatin. The mixture is dried and ground to a fine powder. The Avicel and then the magnesium stearate are admixed with the granulation. This is then compressed in a tablet press to form 1000 tablets each containing 100 g. of active ingredient.

EXAMPLE 59

1000 tablets each containing 200 mg. of 1-(3-carboxy-2-methylpropanoyl)-L-proline are produced from the following ingredients:

| | |
|---|---|
| 1-(3-Carboxy-2-methylpropanoyl)-L-proline | 200 g. |
| Lactose | 100 g. |
| Avicel | 150 g. |
| Corn starch | 50 g. |

-continued

| | |
|---|---|
| Magnesium stearate | 5 g. |

The 1-(3-carboxy-2-methylpropanoyl)-L-proline, lactose and Avicel are admixed, then blended with the corn starch. Magnesium stearate is added. The dry mixture is compressed in a tablet press to form 1000 505 mg. tablets each containing 200 mg. of active ingredient. The tablets are coated with a solution of Methocel E 15 (methyl cellulose) including as a color a lake containing yellow #6.

EXAMPLE 60

Two piece #1 gelatin capsules each containing 250 mg. of 1-(4-carboxy-2-methylbutanoyl)-L-proline are filled with a mixture of the following ingredients:

| | |
|---|---|
| 1-(4-Carboxy-2-methylbutanoyl)-L-proline | 250 mg. |
| Magnesium stearate | 7 mg. |
| USP lactose | 193 mg. |

EXAMPLE 61

An injectable solution is produced as follows:

| | |
|---|---|
| 1-(4-Carboxybutanoyl)-L-Proline | 500 g. |
| Methyl paraben | 5 g. |
| Propyl paraben | 1 g. |
| Sodium chloride | 25 g. |
| Water for injection qs. | 5 l. |

The active substance, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains 5 ml. of solution in a concentration of 100 mg. of active ingredient per ml. of solution for injection.

What is claimed is:

1. A compound of the formula

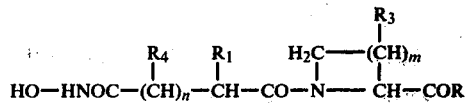

wherein
R is hydroxy, amino or lower alkoxy;
$R_1$ and $R_4$ each is hydrogen, lower alkyl or phenyl-lower alkyl;
$R_3$ is hydrogen, hydroxy or lower alkyl;
m is 3;
n is 0, 1 or 2
and basic salts thereof.

2. A compound as in claim 1 wherein R is hydroxy; $R_1$ is hydrogen or lower alkyl; $R_3$ and $R_4$ each is hydrogen; and n is 1 or 2.

3. A compound as in claim 1 wherein $R_3$ and $R_4$ each is hydrogen.

4. A compound as in claim 1 wherein n is 1.

5. A compound as in claim 1 wherein n is 2.

6. A compound as in claim 1 wherein R is hydroxy.

7. A compound as in claim 1 wherein $R_1$ is hydrogen or methyl.

8. A compound as in claim 1 in which the pipecolic acid is in the L-form.

9. A compound as in claim 6 wherein $R_1$ is methyl, $R_3$ is hydrogen and n is 0.

10. A compound as in claim 6 wherein $R_1$ is methyl, $R_3$ and $R_4$ each is hydrogen and n is 1.

11. A compound as in claim 6 wherein $R_1$ is methyl, $R_3$ and $R_4$ each is hydrogen and n is 2.

12. A compound as in claim 6 wherein $R_1$ is methyl, $R_3$ is 5-hydroxy, $R_4$ is hydrogen and n is 1.

13. A compound as in claim 6 wherein $R_1$ is methyl, $R_3$ is 5-hydroxy, $R_4$ is hydrogen and n is 2.

* * * * *